United States Patent
Wada

(10) Patent No.: US 11,185,517 B2
(45) Date of Patent: Nov. 30, 2021

(54) PHARMACEUTICAL COMPOSITION FOR TREATMENT OR REMISSION OF CHRONIC MYELOGENOUS LEUKEMIA

(71) Applicant: Delta-Fly Pharma, Inc., Tokushima (JP)

(72) Inventor: Hiromi Wada, Kyoto (JP)

(73) Assignee: DELTA-FLY PHARMA, INC., Tokushima (JP)

( * ) Notice: Subject to any disclaimer, the term of this patent is extended or adjusted under 35 U.S.C. 154(b) by 88 days.

(21) Appl. No.: 16/684,091

(22) Filed: Nov. 14, 2019

(65) Prior Publication Data

US 2020/0078322 A1 Mar. 12, 2020

Related U.S. Application Data

(63) Continuation of application No. 16/342,429, filed as application No. PCT/JP2017/037338 on Oct. 16, 2017, now abandoned.

(30) Foreign Application Priority Data

Oct. 17, 2016 (JP) .................... 2016-203662

(51) Int. Cl.
| | |
|---|---|
| *A61K 31/165* | (2006.01) |
| *A61K 9/00* | (2006.01) |
| *A61P 35/02* | (2006.01) |
| *A61K 31/506* | (2006.01) |
| *A61P 43/00* | (2006.01) |

(52) U.S. Cl.
CPC .......... *A61K 31/165* (2013.01); *A61K 9/0053* (2013.01); *A61K 31/506* (2013.01); *A61P 35/02* (2018.01); *A61P 43/00* (2018.01)

(58) Field of Classification Search
None
See application file for complete search history.

(56) References Cited

U.S. PATENT DOCUMENTS

2018/0256668 A1   9/2018   Wada

FOREIGN PATENT DOCUMENTS

| TW | 201628608 A | 8/2015 |
|---|---|---|
| WO | WO 2016/098546 A1 | 6/2016 |

OTHER PUBLICATIONS

Demizu et al., "Development of BCR-ABL degradation inducers via the conjugation of an imatinib derivative and a cIAP1 ligand", Bioorganic & Medicinal Chemistry Letters, vol. 26, 2016 (Available online Sep. 15, 2016). pp. 4865-4869.
Extended European Search Report dated Aug. 26, 2020 for Application No. 17861731.2.
Ota et al., "Clinical trials of bestatin for leukemia and solid tumors", Biotherapy, vol. 4, 1992, pp. 205-214.
Aoki et al., "Hyperuricemia in Child and Urine alkalizing therapy— Effect of CG-120 on Lesch-Nyhan syndrome and infantile leukemia", Shinyaku-To-Rinsho (Journal of New Remedies & Clinics), vol. 30, No. 1, 1981, p. 71-75, with partial translation.
International Search Report for PCT/JP2017/037338 (PCT/ISA/210) dated Dec. 12, 2017.
Ishii et al., "One case that there was efficacy by combination of BMT re-therapy with Imatinib mesilate therapy for a CML patient having relapse after long-term remission", The Japanese Journal of Pediatric Hematology, vol. 17, No. 4, 2003, p. 261, with partial translation.
Kinoshita et al., "Urine alkalizing therapy and tubular resorption for hematopoietic malignant tumor in childhood", Shoni-Gan (Cancer in Child), vol. 30, No. 1, 1993, p. 7-13, with partial translation.
Medication Interview Form, "Prescription Medication, Antineoplastic Agent Bestatin Capsule 10 mg, Bestatin Capsule 30 mg", Nippon Kayaku Co., Ltd., Jun. 2012 (revised 5th edition), 48 pages, with partial translation.
Medication Interview Form, "Antineoplastic Agent (Tyrosine Kinase Inhibitor) Glivec® Tablet 100 mg, Imatinib Mesylate Tablet", Novartis Pharma K. K., revised on Jul. 2017 (12th edition) with May 2018 (13th edition), 103 pages, with partial translation.
Office Action for Taiwanese Patent Application No. 106135262 dated May 30, 2018.
Sawafuji et al., "Aminopeptidase Inhibitors Inhibit Proliferation and Induce Apoptosis of K562 and STI571-resistant K562 Cell Lines Through the MAPK and GSK-3β Pathways", Leukemia & Lymphoma, vol. 44, No. 11, Nov. 2003, pp. 1987-1996.
Sawafuji et al., "Effects of Aminopeptidase Inhibitors on STI571 Resistant CML Cell Lines", Blood, vol. 98, No. 11, 2001, p. 309a, abstract# 1306.
Thomas et al., "Treatment of Philadelphia chromosome-positive acute lymphocytic leukemia with hyper-CVAD and imatlnib mesylate", Blood, vol. 103, No. 12, Jun. 15, 2004, p. 4396-4407.
Written Opinion of the International Searching Authority for PCT/JP2017/037338 (PCT/ISA/237) dated Dec. 12, 2017.

*Primary Examiner* — Brian J Davis
(74) *Attorney, Agent, or Firm* — Birch, Stewart, Kolasch & Birch, LLP

(57) ABSTRACT

The present application provides a pharmaceutical composition for use in treatment or remission of patients with chronic myelogenous leukemia, wherein the composition comprises, as active ingredients, (2S)-2-[(2S,3R)-3-amino-2-hydroxy-4-phenylbutanoylamino]-4-methylpentanoic acid or a pharmacologically acceptable salt thereof, and 4-[(4-methyl-1-piperazinyl)methyl]-N-[4-methyl-3-[[4-(3-pyridinyl)-2-pyrimidinyl]amino]phenyl]-benzamide or a pharmacologically acceptable salt thereof, both of which are used at low doses.

6 Claims, 1 Drawing Sheet

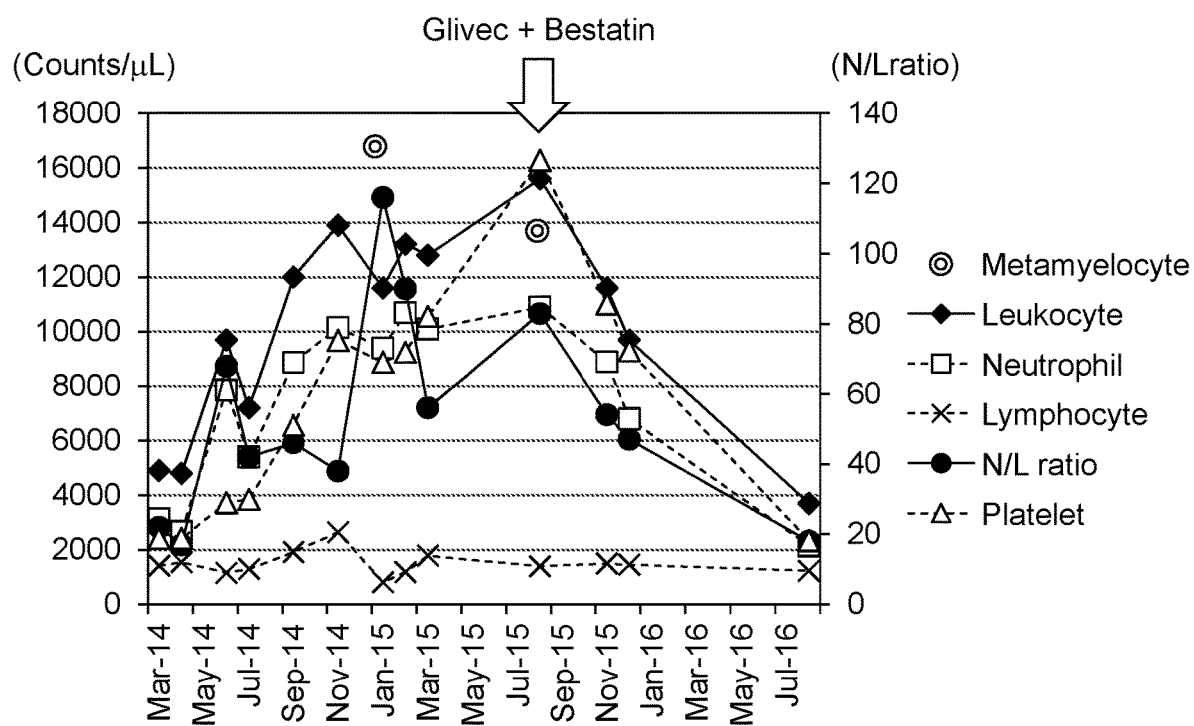

PHARMACEUTICAL COMPOSITION FOR TREATMENT OR REMISSION OF CHRONIC MYELOGENOUS LEUKEMIA

CROSS REFERENCE TO RELATED APPLICATIONS

This application is a Continuation of copending application Ser. No. 16/342,429, filed on Apr. 16, 2019, which is a national phase of PCT International Application No. PCT/JP2017/037338 filed on Oct. 16, 2017, which claims the benefit under 35 U.S.C. 119(a) to Patent Application No. 2016-203662, filed in Japan on Oct. 17, 2016, all of which are hereby expressly incorporated by reference into the present application.

TECHNICAL FIELD

The present invention relates to a pharmaceutical composition for use in the treatment or remission of patients with chronic myelogenous leukemia, wherein the composition comprises, as active ingredients, (2S)-2-[(2S,3R)-3-amino-2-hydroxy-4-phenylbutanoylamino]-4-methylpentanoic acid or a pharmacologically acceptable salt thereof, and 4-[(4-methyl-1-piperazinyl)methyl]-N-[4-methyl-3-[[4-(3-pyridinyl)-2-pyrimidinyl]amino]phenyl]-benzamide or a pharmacologically acceptable salt thereof.

BACKGROUND ART

Chronic myelogenous leukemia (CML) is a kind of hematologic malignancy, which develops due to neoplastic transformation of hematopoietic stem cells and causes a marked increase in leukocytes.

At present, Glivec (or Gleevec; registered trademark) has been used as a first-line drug for the treatment of chronic myelogenous leukemia (Non Patent Literature 1). Glivec comprises, as an active ingredient, 4-[(4-methylpiperazin-1-yl)methyl]-N-[4-methyl-3-[(4-pyridin-3-ylpyrimidin-2-yl)amino]phenyl]benzamide monomethanesulfonate (generic name: imatinib mesylate), and can selectively inhibit the activity of Bcr-Abl tyrosine kinase, which is associated with deterioration of chronic myelogenous leukemia.

On the other hand, the administering Glivec for treatment of chronic myelogenous leukemia does not radically treat the disease, but merely alleviates the chronic symptoms thereof. Thus, the patients need to be administered with Glivec for a long period of time. However, since the recommended daily dose of Glivec is as relatively high as 400 mg to 600 mg, the long-term administration of Glivec imposes economic burden on patients, and also, easily develops adverse effects.

Under such circumstances, there are needs for a new therapy of chronic myelogenous leukemia, reducing economic and physical burden on patients.

It is known that Bestatin (registered trademark) comprises, as an active ingredient, (2S)-2-[(2S,3R)-3-amino-2-hydroxy-4-phenylbutanoylamino]-4-methylpentanoic acid (generic name: ubenimex), which binds to aminopeptidase existing on the surface of immunocompetent cells and exhibits immune-enhancing action on cancer patients. Bestatin has been approved by the authorities in Japan regarding its application for extension of a survival period by combination with a drug for maintenance and consolidation therapy after the remission induction therapy for adult acute non-lymphocytic leukemia, and at present, Bestatin has been clinically applied (Non Patent Literature 2). Moreover, to date, the present inventors have been reported that elderly cancer patients or terminal cancer patients can be treated or alleviated by administration of a low dose of Bestatin (10 mg/day) (Patent Literature 1).

PRIOR ART LITERATURE

Patent Literature

Patent Literature 1: International Publication WO2016/098546

Non Patent Literature

Non Patent Literature 1: Medication Interview Form, "Antineoplastic Agent (Tyrosine Kinase Inhibitor) Glivec® Tablet 100 mg, Imatinib Mesylate Tablet" (Novartis Pharma K. K., revised on July 2017 (12th edition))

Non Patent Literature 2: Medication Interview Form "Prescription Medication, Antineoplastic Agent Bestatin Capsule 10 mg, Bestatin Capsule 30 mg" (Nippon Kayaku Co., Ltd., June 2012 (revised 5th edition))

SUMMARY OF INVENTION

Problem to be Solved by the Invention

An object of the present invention is to provide a novel method for treatment of chronic myelogenous leukemia, which method reduces economic and physical burden on patients.

Solution to Problem

Through intensive studies to solve the above-mentioned problem, the present inventors have now found that Bestatin, which has been clinically applied for extension of a survival period in combination with a drug for maintenance and consolidation therapy after the remission induction therapy for adult acute non-lymphocytic leukemia, is administered at a dose much lower than its general dose (which is 30 to 60 mg/body/day), and Glivec, which has been used in treatment of chronic myelogenous leukemia, is also administered at a dose much lower than its general dose (which is 400 to 600 mg/body/day), to the patients with chronic myelogenous leukemia, so that the combination administration of the two drugs is effective for treatment and/or remission of the patients with chronic myelogenous leukemia. The present invention is based on these findings.

The present invention is as follows.

[1] A pharmaceutical composition for use in treatment or remission of a patient with chronic myelogenous leukemia, wherein the composition comprises, as active ingredients, (2S)-2-[(2S,3R)-3-amino-2-hydroxy-4-phenylbutanoylamino]-4-methylpentanoic acid or a pharmacologically acceptable salt thereof, and 4-[(4-methyl-1-piperazinyl)methyl]-N-[4-methyl-3-[[4-(3-pyridinyl)-2-pyrimidinyl]amino]phenyl]-benzamide or a pharmacologically acceptable salt thereof.

[2] The pharmaceutical composition according to the above [1], characterized in that the composition is used to administer (2S)-2-[(2S,3R)-3-amino-2-hydroxy-4-phenylbutanoylamino]-4-methylpentanoic acid or a pharmacologically acceptable salt thereof at a dose of 5 to 20 mg/day and 4-[(4-methyl-1-piperazinyl)methyl]-N-[4-methyl-3-[[4-(3-pyridinyl)-2-pyrimidinyl]amino]phenyl]-benzamide or a pharmacologically acceptable salt thereof at a dose of 50 to 200 mg/day, respectively, to the patient one to three times a day.

[3] The pharmaceutical composition according to the above [1] or [2], characterized in that the composition is used to administer (2S)-2-[(2S,3R)-3-amino-2-hydroxy-4-phenylbutanoylamino]-4-methylpentanoic acid or a pharmacologically acceptable salt thereof at a dose of 10 mg/day and 4-[(4-methyl-1-piperazinyl)methyl]-N-[4-methyl-3-[[4-(3-pyridinyl)-2-pyrimidinyl]amino]phenyl]-benzamide or a pharmacologically acceptable salt thereof at a dose of 100 mg/day, respectively, to the patient one to three times a day.

[4] The pharmaceutical composition according to the above [2] or [3], wherein the administering is oral administration.

[5] The pharmaceutical composition according to any one of the above [1] to [4], wherein the patient is in a range from neutral to alkaline with regard to pH value of the urine.

[6] The pharmaceutical composition according to any one of the above [1] to [5], which comprises the two active ingredients in the form of a compounding agent.

[7] The pharmaceutical composition according to any one of the above [1] to [5], which comprises the two active ingredients in the form of a kit preparation.

According to the present invention, a novel therapeutic method with little adverse effect for patients having chronic myelogenous leukemia, can be provided.

The present description includes the contents as disclosed in Japanese Patent Application No. 2016-203662 from which the present application claims priority.

BRIEF DESCRIPTION OF DRAWINGS

The FIGURE is a graph showing changes in the metamyelocyte count, leukocyte count, neutrophil count, platelet count, lymphocyte count, and the ratio of neutrophil count and lymphocyte count (N/L ratio) in the peripheral blood, depending on the combination therapy of using Glivec and Bestatin at low doses on patients with chronic myelogenous leukemia.

MODES FOR CARRYING OUT THE INVENTION

The present invention will be further specifically described.

The present invention relates to a pharmaceutical composition for use in the treatment or remission of a patient with chronic myelogenous leukemia, wherein the composition comprises, as active ingredients, (2S)-2-[(2S,3R)-3-amino-2-hydroxy-4-phenylbutanoylamino]-4-methylpentanoic acid or a pharmacologically acceptable salt thereof, and 4-[(4-methyl-1-piperazinyl)methyl]-N-[4-methyl-3-[[4-(3-pyridinyl)-2-pyrimidinyl]amino]phenyl]-benzamide or a pharmacologically acceptable salt thereof.

It is known that (2S)-2-[(2S,3R)-3-amino-2-hydroxy-4-phenylbutanoylamino]-4-methylpentanoic acid is called, as the generic name, "ubenimex" and can be used as an active ingredient of an antineoplastic agent having an efficacy or effect that is extension of a survival period by use of combining with a drug for maintenance and consolidation chemotherapy after the complete remission induction therapy for adult acute non-lymphocytic leukemia. Hereinafter, as used herein, (2S)-2-[(2S,3R)-3-amino-2-hydroxy-4-phenylbutanoylamino]-4-methylpentanoic acid is referred to as "ubenimex."

In the present invention, ubenimex or a pharmacologically acceptable salt thereof may be produced based on general methods known previously. For example, it may be not only a chemically synthesized product, but a product obtained by culturing and fermenting microorganisms (e.g., *Streptomyces olivoreticuli*). Alternatively, commercially available products such as "Bestatin (registered trademark)" may also be used.

Ubenimex is not in the form of a salt, but examples of a pharmacologically acceptable salt of ubenimex may include salts with hydrochloric acid, sulfuric acid, and phosphoric acid.

It is known that 4-[(4-methyl-1-piperazinyl)methyl]-N-[4-methyl-3-[[4-(3-pyridinyl)-2-pyrimidinyl]amino]phenyl]-benzamide can be used as an active ingredient of an antineoplastic drug having efficacy or effects on chronic myelogenous leukemia, KIT (CD117)-positive gastrointestinal stromal tumor, Philadelphia chromosome-positive acute lymphocytic leukemia, and FIP1L1-PDGFRα-positive hypereosinophilic syndrome or chronic eosinophilic leukemia. Hereinafter, as used herein, the pharmacologically acceptable salt thereof is not particularly limited, but the form of a monomethanesulfonate is known and is generally used. Hereinafter, as used herein, 4-[(4-methyl-1-piperazinyl)methyl]-N-[4-methyl-3-[[4-(3-pyridinyl)-2-pyrimidinyl]amino]phenyl]-benzamide is referred to as "imatinib," and the monomethanesulfonate thereof is referred to as "imatinib mesylate."

In the present invention, imatinib or a pharmacologically acceptable salt thereof, which is chemically synthesized by general methods known previously (e.g., U.S. Pat. No. 5,521,184, WO03/066613, U.S. Pat. No. 6,894,051, etc.), may be used. Alternatively, commercially available products such as "Glivec (registered trademark)" (imatinib mesylate) or the like may also be used.

In the pharmaceutical composition of the present invention, ubenimex or a pharmacologically acceptable salt thereof and imatinib or a pharmacologically acceptable salt thereof may be contained in the composition in amounts within the ranges described below suitable for administration to patients. That is, ubenimex or a pharmacologically acceptable salt thereof may be contained in the composition in an amount appropriately selected from the range of 1 to 20 mg, 1 to 10 mg, or 1 to 5 mg, and imatinib or a pharmacologically acceptable salt thereof may be contained in the composition in an amount appropriately selected from the range of 1 to 200 mg, 1 to 100 mg, or 1 to 50 mg. For example, the pharmaceutical composition of the present invention may comprise 10 mg of the ubenimex or pharmacologically acceptable salt thereof, and 100 mg of the imatinib or pharmacologically acceptable salt thereof.

The pharmaceutical composition of the present invention may also comprise an excipient, a binder, a disintegrator, a lubricant, a diluent, a solubilizer, a suspending agent, a tonicity agent, a pH adjuster, a buffer agent, a stabilizer, a coloring agent, a corrigent, a flavoring agent, etc., which are conventionally used in the production of medicaments, together with ubenimex or a pharmacologically acceptable salt thereof and imatinib or a pharmacologically acceptable salt thereof, which are used as active ingredients. The pharmaceutical composition of the present invention may be processed into a dosage form that is suitable for oral administration or parenteral administration (e.g., intravenous administration, intra-arterial administration, topical administration using injection, intraperitoneal or intrathoracic administration, transpulmonary administration, subcutaneous administration, intramuscular administration, sublingual administration, transdermal administration, or intrarectal administration, etc.). Examples of the possible dosage form of the pharmaceutical composition of the present invention may include a solution agent, an emulsion, a liposome preparation, an injection agent, a suspending agent, an ointment, a cream agent, a percutaneous absorption agent, a transmucosal absorption agent, a tablet, a pill, a capsule, a powder agent, a powdery agent, a granule agent, a fine granule agent, and a syrup agent, but are not limited thereto. These dosage forms can be each formulated, molded or prepared according to methods conventionally used in the present technical field. Moreover, the pharmaceutical composition of the present invention may be freeze-dried so that it becomes in an easily preservable state, and subsequently, the composition may be dissolved in a diluent such as water, physiological saline, or buffer to adjust at an appropriate concentration, when used.

The pharmaceutical composition of the present invention may be in the form of a compounding agent that comprises both ubenimex or a pharmacologically acceptable salt thereof and imatinib or a pharmacologically acceptable salt thereof as active ingredients, or may also be in the form of a kit preparation in which ubenimex or a pharmacologically acceptable salt thereof and imatinib or a pharmacologically acceptable salt thereof used as active ingredients are accommodated into a single package suitable for combination administration. Herein, the term "combination administration" includes not only a case where ubenimex or a pharmacologically acceptable salt thereof and imatinib or a pharmacologically acceptable salt thereof are concurrently administered to a patient, but also a case where ubenimex or a pharmacologically acceptable salt thereof and imatinib or a pharmacologically acceptable salt thereof are administered to a patient with a certain interval, in a range in which the two active ingredients can concurrently act on the patient. Moreover, in such "combination administration," the administration route and the administration means of ubenimex or a pharmacologically acceptable salt thereof may be identical to or different from those of imatinib or a pharmacologically acceptable salt thereof.

The pharmaceutical composition of the present invention can be administered to patients with chronic myelogenous leukemia for the purpose of treating or alleviating chronic myelogenous leukemia.

Chronic myelogenous leukemia may be in any stage of a chronic stage, a transitional stage, and an acute stage, and the stage of the disease is not particularly limited.

The patient with chronic myelogenous leukemia who is an administration target of the pharmaceutical composition of the present invention is preferably a patient that the pH value of her/his urine is in a range from neutral to alkaline. Such a patient can be confirmed using the pH value of urine as the indicator. Therefore, the patient with chronic myelogenous leukemia who can be an administration target of the pharmaceutical composition of the present invention is a patient that the pH value of her/his urine is in a range from neutral to alkaline. The patient is a mammal including human, preferably human.

There is a case where the pH value of urine of a cancer patient is on the acidic side. In this case, the urine pH value can be adjusted to a range from neutral to alkaline (i.e., thereby, physical conditions can be improved) by ingestion or administration of the following one or more substances. Examples of such substances include brightly colored vegetables, edible baking soda, alkalizing therapy agents (potassium citrate-sodium citrate hydrate containing agent (Uralyt (registered trademark))), and the like. The pH value of urine can be adjusted to a range from neutral to alkaline by ingesting, for example, brightly colored vegetables in an amount of approximately 350 g per day, or edible baking soda in an of 3 g per day, about three times a day, or alternatively ingesting an alkalizing therapy agent in an amount of 2 g per day, about three to four times a day. It is preferable that the improvement of physical conditions be continuously carried out until the pH value of the urine of a patient is adjusted to a range from neutral to alkaline.

The dose and times of administration of the pharmaceutical composition of the present invention to patients with chronic myelogenous leukemia may be varied depending on factors such as ages and body weights of the patients, the severity of the disease, and the like. The dose of ubenimex or a pharmacologically acceptable salt thereof used as the active ingredient may be appropriately selected from 1 to 20 mg/body/day, 1 to 10 mg/body/day, 5 to 15 mg/body/day, and the like, or from total daily doses that are 5 to 20 mg, 7 to 15 mg, 8 to 13 mg, 10 mg, and the like. Also, the dose of imatinib or a pharmacologically acceptable salt thereof used as an active ingredient may be appropriately selected from 1 to 200 mg/body/day, 1 to 100 mg/body/day, 50 to 150 mg/body/day, and the like, or from total daily doses that are 50 to 200 mg, 70 to 150 mg, 80 to 130 mg, 100 mg, and the like. And in this context, the above drugs can be each administered, in the above-mentioned doses, to the patients, 1-3 times a day, every day, or every 1-21 days. For example, when the pharmaceutical composition of the invention can be administered with little or no adverse effects to a patient once a day, at a dose of ubenimex or a pharmacologically acceptable salt thereof that is 10 mg, and at a dose of imatinib or a pharmacologically acceptable salt thereof that is 100 mg, and, as a result, therapeutic and improvement effects can also be achieved.

In general, for the purpose of maintenance and consolidation after the complete remission induction therapy for adult acute non-lymphocytic leukemia, ubenimex is used once a day at a dose of 30 mg, when used in combination with a chemotherapeutic agent (Non Patent Literature 2). On the other hand, imatinib or a pharmacologically acceptable salt thereof is generally used to a patient with chronic myelogenous leukemia once a day at a dose of 400 mg to 600 mg, or at a dose of 800 mg per day (at a single dose of 400 mg twice a day) (Non Patent Literature 1).

Therefore, according to the pharmaceutical composition of the present invention, ubenimex or a pharmacologically acceptable salt thereof and imatinib or a pharmacologically acceptable salt thereof can be each used at a dose that is much lower than the dose previously applied to patients with chronic myelogenous leukemia.

The effects of the pharmaceutical composition of the present invention can be evaluated using one or a plurality of indicators of the following (i) to (vii) regarding patients administered with the present pharmaceutical composition, in comparison to patients who are not administered with the present pharmaceutical composition or patients before administration.

(i) The metamyelocyte count in peripheral blood is decreased or disappeared.
(ii) The leukocyte count in peripheral blood is decreased.
(iii) The neutrophil count in peripheral blood is decreased.
(iv) The platelet count in peripheral blood is decreased.
(v) The ratio (NLR) of neutrophil count (N) and lymphocyte count (L) in peripheral blood is decreased.
(vi) The ratio (PLR) of platelet count (P) and lymphocyte count (L) in peripheral blood is decreased.
(vii) Extension of survival period (i.e., life-prolonging effect) is observed.

The pharmaceutical composition of the present invention can be administered to a patient, together with an existing therapeutic agent for chronic myelogenous leukemia, where needed. Examples of such an existing therapeutic agent include dasatinib (trade name: Sprycel (registered trademark)), bosutinib (trade name: Bosulif (registered trademark)), and nilotinib (trade name: Tasigna (registered trademark)), but are not limited thereto.

The present invention further relates to a method for treating or alleviating patients with chronic myelogenous leukemia, using the above-described pharmaceutical composition of the present invention. The patients with chronic myelogenous leukemia who can be treated or alleviated by the present method, and the usage and dose of the pharmaceutical composition of the invention are as described above.

EXAMPLES

Hereinafter, the present invention will be described in more detail with reference to examples as described below. However, these examples are not intended to limit the scope of the present invention.

Example 1: Combination Administration of Glivec and Bestatin at Low Doses

To a 71-year-old female patient with chronic myelogenous leukemia, Tasigna (registered trademark) (nilotinib) was administered from Jan. 9, 2014. However, since strong adverse effects were observed, administration of the drug was stopped after 5 days of administration.

Thus, from August 2015, the patient was taught to improve her physical conditions by ingestion of brightly colored vegetables (350 g/day), or administration with edible baking soda (3 g×3 times/day), or administration with Uralyt (a compounding agent of potassium citrate and sodium citrate hydrate) (2 g×3-4 times/day), or the like (indicator: conversion of her urine pH to a range from neutral to alkaline), and both Glivec (100 mg/day) and Bestatin (10 mg/day) were administered to the patient at the doses much lower than general doses for Glivec and Bestatin, by combination administration. This combination therapy using Glivec and Bestatin was carried out for about 1 year until July 2016.

As a result (see the FIGURE), the disappearance of metamyelocytes was observed in the peripheral blood of the patient with chronic myelogenous leukemia. In addition, it was observed that the leukocyte count, neutrophil count, platelet count, and the ratio of neutrophil count and lymphocyte count (N/L ratio), were all significantly decreased in the peripheral blood of the patient.

Since the metamyelocyte, a kind of blast, was observed in the peripheral blood of the present patient, she was considered to be at the acute stage of chronic myelogenous leukemia. The initially administered Tasigna (registered trademark) (nilotinib) had been developed as a therapeutic agent for the transitional stage of chronic myelogenous leukemia from the chronic stage to the acute stage. However, no therapeutic effect of this drug was found in the present patient. On the other hand, it was known that Glivec did not have sufficient effects on chronic myelogenous leukemia that is at the transitional stage or at the acute stage.

In contrast, the present inventors have now found that the low dose-combination therapy, in which a low dose of Bestatin is used together with a low dose of Glivec, has therapeutic effects on chronic myelogenous leukemia (more specifically, the chronic myelogenous leukemia that is not at the chronic stage on which Glivec did not seem to have sufficient therapeutic effects), and that the low dose-combination therapy also has the effect of improving the conditions or symptoms of the patient.

Furthermore, the low dose-combination therapy of using Glivec and Bestatin was not found to cause clinical adverse effects, and thus, it was demonstrated that the low dose-combination therapy of using Glivec and Bestatin is a favorable therapy for patients with chronic myelogenous leukemia, not causing adverse effects.

Furthermore, the urine pH of the patient was acidic (pH less than 7) before the improvement of her physical conditions, but the urine pH of the patient was in a range from neutral to alkaline (pH 7.0-7.5) after the improvement of her physical conditions.

From the aforementioned results, it was confirmed that the combination therapy of using Glivec and Bestatin at low doses is an effective therapeutic method for patients with chronic myelogenous leukemia.

INDUSTRIAL APPLICABILITY

Since the present invention provides a combination therapy of using Glivec and Bestatin at low doses on patients with chronic myelogenous leukemia, it is possible to improve the conditions or symptoms of the patients, while reducing burden on the patients. Accordingly, the present invention is industrially useful in the medical field.

All publications, patents, and patent applications cited herein are incorporated herein by reference in their entirety.

The invention claimed is:

1. A method of treating a patient with chronic myelogenous leukemia that is at the transitional stage or at the acute stage, characterized in that the method comprises administering to the patient a pharmaceutical composition or kit preparation that comprises the following active ingredients:
   (i) (2S)-2-[(2S,3R)-3-amino-2-hydroxy-4-phenylbutanoylamino]-4-methylpentanoic acid or a pharmacologically acceptable salt thereof, and
   (ii) 4-[(4-methyl-1-piperazinyl)methyl]-N-[4-methyl-3-[[4-(3-pyridinyl)-2-pyrimidinyl] amino]phenyl]-benzamide or a pharmacologically acceptable salt thereof,
   wherein the active ingredient (i) is administered at a dose of 10 mg/day, and the active ingredient (ii) is administered at a dose of 50 to 200 mg/day, respectively, to the patient one to three times a day.

2. The method according to claim 1, wherein the active ingredient (i) is administered at a dose of 10 mg/day and the active ingredient (ii) is administered at a dose of 100 mg/day, respectively, to the patient one to three times a day.

3. The method according to claim 1, wherein the active ingredients (i) and (ii) are orally administered.

4. The method according to claim 1, wherein in the patient the urine pH value is adjusted to a range from neutral to alkaline prior to or concurrently with administering the active ingredient (i) and the active ingredient (ii).

5. The method according to claim 1, wherein the pharmaceutical composition comprises the active ingredients (i) and (ii) in the form of a compounding agent.

6. The method according to claim 1, wherein the active ingredients (i) and (ii) in the kit preparation are administered to the patient with an interval(s).

* * * * *